Figure 1:
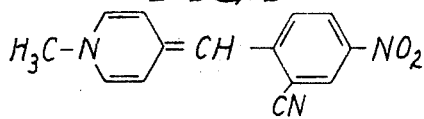
Figure 2:
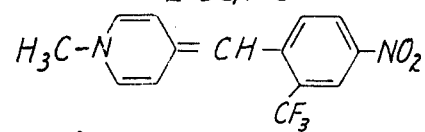

United States Patent [19]

Brown

[11] 4,033,948

[45] July 5, 1977

[54] ACUTANCE AGENTS FOR USE IN THERMALLY-DEVELOPABLE PHOTOSENSITIVE COMPOSITIONS

[75] Inventor: Harvey A. Brown, Lake Elmo, Minn.

[73] Assignee: Minnesota Mining and Manufacturing Company, St. Paul, Minn.

[22] Filed: May 17, 1976

[21] Appl. No.: 687,003

[52] U.S. Cl. .............................. 260/240 A; 96/101; 96/114.1; 260/240 F; 260/240 D; 260/240.9
[51] Int. Cl.$^2$ .............. C07D 207/30; C07D 215/00
[58] Field of Search ........ 260/240.9, 240 A, 240 F; 96/114.1, 101

[56] References Cited

UNITED STATES PATENTS 3,652,288   3/1972   Fumia et al. .................. 260/240.9

FOREIGN PATENTS OR APPLICATIONS 1,399,751   7/1975   United Kingdom

OTHER PUBLICATIONS

Sheppard, J. Am. Chem. Soc. 85 (1963), pp. 1314–1318.

*Primary Examiner*—Arthur P. Demers
*Attorney, Agent, or Firm*—Cruzan Alexander; Donald M. Sell; Temple Clayton

[57] ABSTRACT

Certain members of the class of odd-numbered methine arylidene dye bases are found to be of use in thermally-developable photosensitive compositions and thermally-developable photosensitive elements containing such agents. These compounds are acutance agents which are relatively stable against photo-bleaching but undergo thermochemical bleaching on heating in silver salt-containing thermally-developable photosensitive compositions.

3 Claims, 16 Drawing Figures

ACUTANCE AGENTS FOR USE IN THERMALLY-DEVELOPABLE PHOTOSENSITIVE COMPOSITIONS

This invention relates to methine cyanine dyes and particularly to methine arylidene dyes having an odd number of methine groups which are further substituted on an aryl group attached to the methine chain by a substituent having a Hammet (para) sigma parameter from about 0.45 to about 0.63. These dyes are found to be valuable in thermally developable photographic and reproduction materials.

DESCRIPTION OF THE PRIOR ART

Prior art teaches the use of acutance (and antihalation) agents in photographic materials to enhance the sharpness of images in photographic materials. They function by absorbing light which is reflected or refracted either at surface interfaces of the photographic materials or in the body of the photographic materials. Unabsorbed reflected or refracted light degrades the image and thereby causes reduced resolution capability. Generally, an antihalation agent is coated on either or both sides of the support for the photographic material or between layers of photoemulsion. Acutance agents are generally incorporated into one or more of the photosensitive layers. Such acutance and antihalation agents are discharged from wet-processed photographic materials in processing baths such as alkaline photographic developing baths.

One important method of reproduction of images is by thermal development. This method uses no processing liquids and therefore precludes the use of antihalation or acutance agents which have been produced for use in wet-process photographic materials. One such thermal development process is sometimes known as the "dry silver" process. Various aspects of the preparation and use of such materials are described in U.S. Pat. Nos. 3,152,904 and 3,457,075.

Acutance agents for use in thermally-developable photographic materials have been described. In U.S. Pat. No. 3,745,009 there are described acutance agents which are energy-decolorizable and suitable for use in thermally-developable photographic materials but are, however, excessively sensitive to heat during production and coating and may decompose prematurely due to ambient heat.

In U.S. Pat. No. 3,769,019 (3M) there are disclosed acutance agents which are thermally-decolorizable protonic dyes although color may return spontaneously after a period of time.

In British Pat. No. 1,399,751 (corresponding also to DOS 2,242,761 and U.S. priority applications Ser. No. 176,681 Aug. 31, 1971 and Ser. No. 260,618 June 7, 1972), there are disclosed thermally stable, photobleachable o-nitro-substituted arylidene dyestuffs of the general formula:

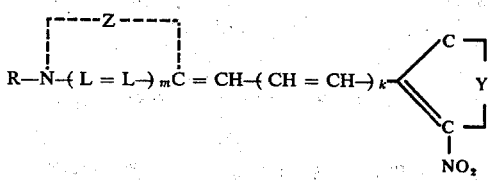

wherein $k = 0$, 1 or 2; $m = 0$ or 1; L is a methine or substituted methine group; R is an alkyl, substituted alkyl, alkenyl, aryl or substituted aryl group; Y represents the atoms necessary to complete mono- or polycyclic aryl group which may be further substituted; and Z represents the atoms necessary to complete a mono- or polycyclic heterocyclic nucleus which may be substituted, the heterocyclic ring containing the nitrogen atom shown being 5 or 6 membered. These dyestuffs may be incorporated in heat developable photographic elements as part of antihalation layer. Such elements may be exposed to a light pattern, thermally developed to provide a sharp image in the element, and then the element fully exposed to light to decolorize the antihalation compounds. Alternatively (DOS, page 21, line 8 ff), the compounds may be incorporated as desensitizers in photosensitive compositions for wet processing.

It is an object and aim of this invention to provide acutance agents for use in dry processing silver reproduction materials and particularly acutance agents which do not tend to desensitize the photosensitive compounds in said reproduction materials. A further object of the invention is to produce acutance agents which bleach thermally under dry processing conditions. Other aims and objects will become apparent hereinelsewhere.

In accordance with these and other aims and objects of the invention, there are provided acutance agents for use in thermally developable, photosensitive compositions. These agents are relatively stable against photobleaching but undergo bleaching on heating in silver salt-containing thermally-developable photosensitive compositions. Furthermore, the acutance agents of the invention do not desensitize thermally-developable photosensitive compositions in the 350 to 450 nm. range of the spectrum. There are also provided storage-stable, thermally developable, photosensitive compositions containing such acutance agents.

The arylidene dye bases of the invention have the general formula:

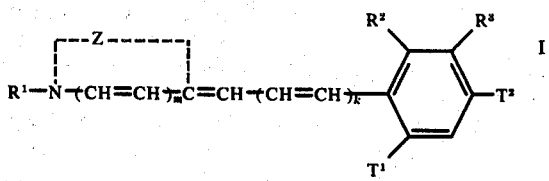

wherein:
Z represents the atoms necessary to complete a mono- or polycyclic dihydroheterocyclic nucleus having 5 to 6 atoms in the ring including the N of the formula and preferred arylidene dye bases which are acutance agents include these in which Z is —CH=CH—, —CH=CH—CH=CH—,

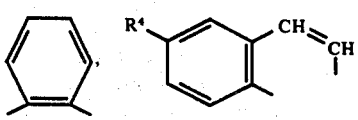

where $R^4$ is H, alkyl of 1–2 carbon atoms or alkoxy of 1–2 carbon atoms,
$R^1$ is an alkyl, substituted alkyl, alkenyl, or aryl group;
$m$ is 0 or 1;
$k$ is 0, 1 or 2;
$T^1$ is an aprotic electron-withdrawing group having a $\sigma_{para}$ value of 0.45 to 0.63 and is preferably CF$_3$ or CN;

T$^2$ is an aprotic electron-withdrawing group having a $\sigma_{para}$ value greater than 0.45 and is preferably NO$_2$; and R$^2$ and R$^3$ are hydrogen, or together constitute a condensed carbocyclic aromatic ring.

The term $\sigma_{para}$ as used herein refers to the Hammett (para) sigma parameter, sometimes herein referred to as Hammett value, as defined by Shepard, J. Am. Chem. Soc., Vol. 85, pg. 1314 et seq. (1963).

It will be seen that the acutance agents of the invention are similar formally in many respects to those described in British Pat. No. 1,399,751 and DOS No. 2,242,761 and are obtained by replacing o-nitro-substituent by electron withdrawing groups having lower Hammett para sigma, i.e., ($\sigma_{para}$) values, of from about 0.45 to about 0.63.

The Hammett para sigma parameter of the nitro group is much higher, 0.778, and it is considered surprising that a much better balance of thermal and photosensitive properties can be obtained together with substantially complete loss of desensitizing properties by such a relatively simple formal change in structure. The presence of nitro groups in the 4-position (T$^2$) is, however, not detrimental to the desired properties.

It is found that suitable T$^1$ groups are aprotic electron withdrawing groups having a $\sigma_{para}$ value of 0.45 to 0.63 and include, for example, as preferred groups, CF$_3$ ($\sigma_{para}$ = 0.55) and CN ($\sigma_{para}$ = 0.63). Such values are readily ascertained by reference to reported tables, for example, in Shepard, supra.

Groups having a $\sigma_{para}$ value less than about 0.45 become increasingly resistant to thermal decolorization and groups have a $\sigma_{para}$ value above about 0.63 become increasingly more light unstable.

The acutance agents of the invention are of the class of odd-numbered arylidene dye bases. The preparation of the acutance agents is by methods similar to the generally known methods for preparation of odd-numbered methine cyanine dye bases such as are described in, among other references, Chapter XI, *Cyanine Dyes and Related Compounds* by Hamer, Interscience Publishers (1964).

The monomethine dye bases, i.e. dye bases where k of Formula I above is zero, can be prepared by condensation in the presence of an acid acceptor, e.g., tertiary amine, of a halogenated aromatic compound of the formula:

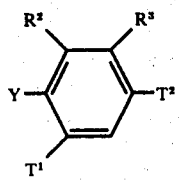

II wherein R$^2$, R$^3$, T$^1$ and T$^2$ are defined as above, and Y is fluorine, chlorine or bromine with a heterocyclic quaternary ammonium compound of the formula:

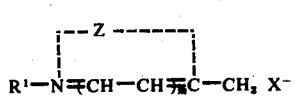

III wherein R$^1$, Z and m are defined above, and X is an anion such as, for example, a halogen ion, a p-toluenesulfonate ion, a fluorosulfonate ion or the like. Generally, the condensation is carried out in an aprotic solvent such as, for example, acetonitrile, benzene or dimethylformamide. Reaction conditions may be from about 50°–150° C for 1 to 3 hours, or as little as a few minutes when unwanted side reactions may occur. The product may be isolated by well known procedures such as crystallization or removal of solvent.

The monomethine dye bases can be prepared by reaction in the presence of an acid acceptor of quaternized heterocyclic compounds having a phenyl- or alkyl-thio substituent in place of the methyl, i.e., of the structure:

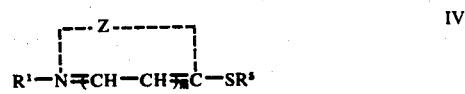

IV where R$^5$ is phenyl or alkyl of 1–4 carbon atoms, with aromatic compounds of the formula:

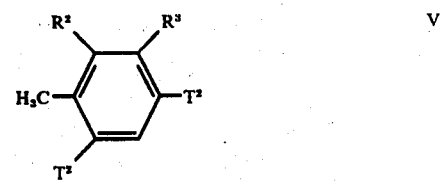

V wherein R$^2$, R$^3$, T$^1$ and T$^2$ are defined as above.

The trimethine dye bases, i.e. those dye bases where k=1 in Formula I above, can be prepared by reaction of a heterocyclic quaternary ammonium compound, e.g., of Formula III above, with diphenylformamidine or an equimolar mixture of diphenylformamidine and triethylorthoformate to give the corresponding β-anilinovinyl derivative:

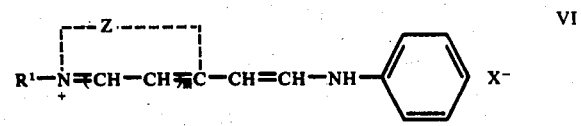

VI where R$^1$, Z, L, X and m are defined above. The β-anilinovinyl derivatives are then caused to condense with an aromatic derivatives are then caused to condense with an aromatic compound such as the aromatic compounds of Formula V to give the trimethine dye bases. Reaction conditions are similar to those used for the preparation of the monomethine dye bases.

The pentamethine dye bases can be prepared in a manner similar to that used for the preparation of the trimethine dye bases using β-anilinoacrolein anil hydrochloride in place of diphenylformamidine to give the corresponding δ-anilinobutadienyl derivative

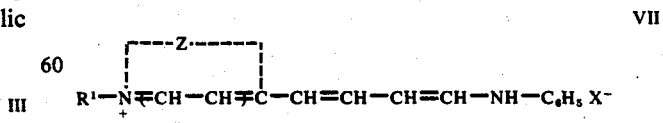

VII wherein R$^1$, Z, X and m are as defined above. The compound of Formula VII is then condensed, under the conditions used for reaction of Compound III, with an aromatic compound of Formula V to yield the pentamethine dye base.

Examples of acutance agents of the invention include the following compounds having the structural formulae of the designated figures shown in the drawings accompanying this specification. The lower case letters on formulae of FIGS. 3, 4, 6, 9 and 15 are positions of protons assigned to infrared absorption peaks.

| FIG. | |
|------|---|
| 1.  | 4-(2-cyano-4-nitrobenzylidene)-1-methyl-1,4-dihydropyridine |
| 2.  | 4-(2-trifluoromethyl-4-nitrobenzylidene)-1-methyl-1,4-dihydropyridine |
| 3.  | 4-(2-cyano-4-nitrobenzylidene)-1-methyl-1,4-dihydroquinoline |
| 4.  | 4-(2-trifluoromethyl-4-nitrobenzylidene)-1-methyl-1,4-dihydroquinoline |
| 5.  | 2-(2-cyano-4-nitrobenzylidene)-1-methyl-1,2-dihydroquinoline |
| 6.  | 2-(2-cyano-4-nitrobenzylidene)-1-ethyl-1,2-dihydroquinoline |
| 7.  | 2-(2-cyano-4-nitrobenzylidene)-1-methyl-6-ethoxy-1,4-dihydroquinoline |
| 8.  | 2-(2-cyano-4-nitrobenzylidene)-1-ethylbenzothiazoline |
| 9.  | 4-(2-cyano-4-nitrobenzylidene)-1-(2-nitrobenzyl)-1,4-dihydropyridine |
| 10. | 2-(2,4-dicyanobenzylidene)-1-ethylbenzoxazoline |
| 11. | 2-(2-cyano-4-nitrobenzylidene)-1-ethylbenzoxazoline |
| 12. | 2-[3-(2-cyano-4-nitrophenyl)allylidene]-1-methyl-1,2-dihydropyridine |
| 13. | 2-[3-(2-cyano-4-nitrophenyl)allylidene]-1-methyl-1,2-dihydroquinoline |
| 14. | 2-[3-(2-cyano-4-nitrophenyl)allylidene]-1-ethyl-1,2-dihydroquinoline |
| 15. | 4-[3-(2-cyano-4-nitrophenyl)allylidene]-1-methyl-1,2-dihydroquinoline |
| 16. | 2-[3-(2-cyano-4-nitrophenyl)allylidene]-1-ethyl-benzothiazoline |
| 17. | 2-[3-(2,4-dicyanonaphthyl-1)allylidene]-1,3-dimethyl-5-ethoxybenzimidazoline |
| 18. | 2-[5-(2-cyano-4-nitrophenyl)pentadiene-2,4-ylidene]-1-methyl-1,2-dihydropyridine |
| 19. | 2-[5-(2-cyano-4-nitrophenyl)pentadiene-2,4-ylidene]-1-ethyl-5-methylbenzothiazoline |
| 20. | 2-[5-(2-cyano-4-nitrophenyl)pentadien-2,4-ylidene]-1-methyl-1,2-dihydroquinoline |
| 21. | 4-(2-cyano-4-nitrobenzylidene)-1-phenyl-1,4-dihydropyridine |
| 22. | 2-(2-cyano-4-nitrobenzylidene)-1-phenylbenzoxazoline |
| 23. | 4-(2-cyano-4-nitrobenzylidene)-1-(4-methoxyphenyl)-1,4-dihydropyridine |
| 24. | 4-[3-(2-cyano-4-nitrophenyl)allylidene]-1-(2-ethoxyethyl)-1,4-dihydropyridine |
| 25. | 4-[ 3-(2-cyano-4-nitrophenyl)allylidene]-1-allyl-1,4-dihydropyridine |
| 26. | 2-(2-cyano-4-nitrobenzylidene)-1-ethyl-6-methoxy-1,2-dihydroquinoline |

The acutance agents of the invention are useful in thermally-developable photosensitive compositions such as those described in U.S. Pat. Nos. 3,457,075, 3,589,901 and 3,589,093. They are optimally used in concentrations of about 0.01 to about 0.1 parts by weight (30 to 300 micromoles) of acutance agent having a molecular weight of about 300 per 100 parts by weight of photosensitive dispersion. The use of more acutance agents in coating an emulsion produces an increase in fog level and increase in residual stain. Lesser amounts are generally found to be ineffective. Preferably about 0.02 to 0.05 parts and more (50 to 150 micromoles) preferably about 0.02 to 0.035 parts (50 to 120 micromoles) of acutance agent having a molecular weight of about 300 is used per 100 parts of photosensitive dispersion. Amounts expressed as micromoles are applicable to acutance agents of the invention in general.

The invention is now further explained by examples showing the preparation and use of acutance agents of the invention. It will be recognized that with complex molecules melting points may be affected by rate of heating, atmosphere and also crystalline forms as well as tendency of the compounds to decompose.

EXAMPLE 1

Figure 3:
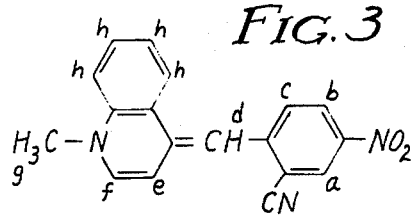

Preparation of 4-(2-cyano-4-nitrobenzylidene)-1-methyl-1,4-dihydroquinoline, FIG. 3.

Lepidine methyl fluorosulfonate (51.4 g., 0.2 moles) and 2-chloro-5-nitrobenzonitrile (36.5 g., 0.2 moles) were dissolved in 350 ml. of dry acetonitrile. The solution was heated to reflux and, while stirring vigorously, triethylamine (40.4 g., 0.4 moles) was added during about 4 minutes. An intense deep purple color developed immediately. The mixture was held at reflux for about one hour and cooled in an ice water bath. The green iridescent crystalline product was collected, washed successively with a small amount of acetonitrile, water, and diethyl ether, and dried at 60° C. There was obtained 35.8 g. (59% of theory) of product having a melting point of 220°–222° C, recrystallized from acetonitrile for analysis:

Calcd. for $C_{18}H_{13}N_3O_2$: %C, 71.3; %H, 4.32; %N, 13.8; Found: %C, 71.3; %H, 4.3; %N, 14.2.

Infrared absorption spectra (IR) and nuclear magnetic resonance spectra (NMR) were consistent with the proposed structure of FIG. 3. NMR peaks expressed as $\delta$ units in parts per million are found at 8.49($a$), 8.23($b$), 8.06($f$), 7.94($c$), 7.3–7.8($h$), 6.87($e$), 6.52($d$), 3.71($g$) the parenthetical letters referring to positions of FIG. 3.

By following the above procedure starting from quinaldine ethylfluorosulfonate there is obtained 2-(2-cyano-4-nitrobenzylidene)-1-ethyl-1,2-dihydroquinoline, m.p. 183°–4° C. Calcd. for $C_{19}H_{15}N_3O_2$: %C, 71.9; %H, 4.76; %N, 13.24 Found: %C, 72.0; %H, 4.80 %N, 13.4 Infrared and nuclear magnetic resonance spectra are in agreement with the structure of FIG. 6. NMR peaks ($\delta$ units in parts per million and corresponding to protons designated by lower case letters in FIG. 6) are found at 8.47($a$), 8.20($b$), 7.75($c$), 7.1–7.6(aromatic protons), 5.70($d$), 4.17($e$) and 1.40($f$).

EXAMPLE 2

Figure 8:
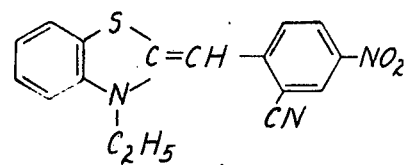

Preparation of 2-(2-cyano-4-nitrobenzylidene)-3-ethylbenzothiazoline, FIG. 8

2-Phenylthiobenzothiazole ethiodide (3.99 g., 0.01 mole) and 2.00 g. (0.012 mole) of 2-cyano-4-nitrotoluene were dissolved in 25 ml. of acetonitrile and then 2.58 g. (0.02 mole) of diisopropyl ethylamine was added. The reaction mixture was refluxed two hours and then cooled for several hours. The green iridescent crystalline product was collected and washed with a small amount of acetonitrile. After drying 1.13 g. of product, m.p. 237°–9° (dec.) was obtained.

Calcd. for $C_{17}H_3N_3O_2S$: %C, 63.1; %H, 4.05; %N, 13.0; Found: %C, 63.0; %H, 4.1; %N, 13.0 IR and NMR were consistent with the structure of FIG. 8.

EXAMPLE 3

Figure 9:
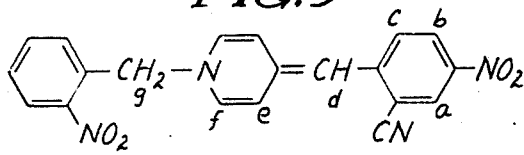
Figure 10:
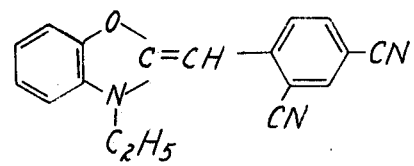
Figure 11:
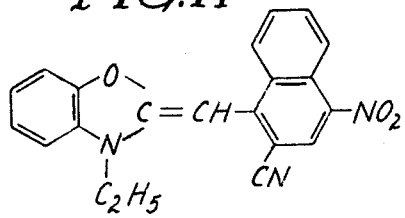
Figure 12:
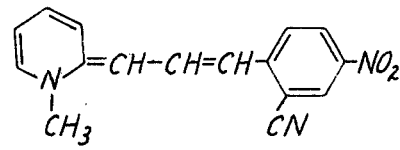
Figure 13:
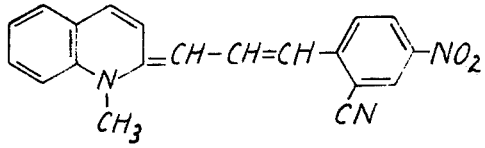

Preparation of 4-(2-cyano-4-nitrobenzylidene)-1-(2-nitrobenzyl)-1,4-dihydropyridine, FIG. 9.

The procedure of Example 1 was repeated using an equivalent, i.e. equimolar, amount of 1-(2-nitrobenzyl)-4-methylpyridinium chloride in place of lepidine methyl fluorosulfonate. A deep blue dye base having m.p. 193°–201° C. was obtained in 47% of theory.

Calcd. for $C_{20}H_{14}N_4O_4$: %C, 64.2; %H, 3.77; %N, 15.0; Found: %C, 63.6; %H, 3.80; %N, 15.3. IR spectra were consistent with the structure of FIG. 9. NMR peaks (δ units in parts per million for the structural features noted in lower case letters in FIG. 9) are found at 8.30(a), 8.20(b), 7.6–8.1(c and other aromatic protons), 7.49(f), 6.90(e), 5.70(d), and 5.47(g).

EXAMPLE 4

Figure 4:
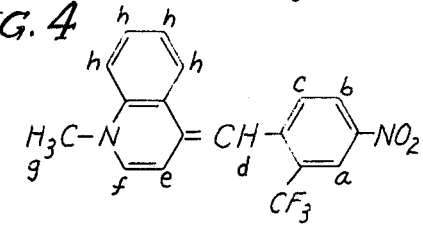
Figure 5:
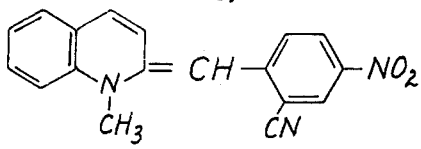
Figure 6:
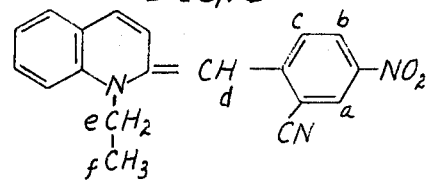
Figure 7:
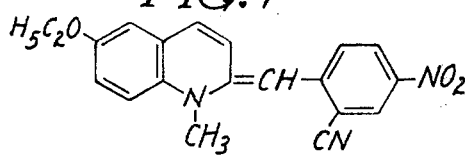

Preparation of 4-(2-trifluoromethyl-4-nitrobenzylidene)-1-methyl-1,4-dihydroquinoline, FIG. 4.

The procedure of Example 1 was repeated using an equivalent amount of 2-chloro-5-nitrobenzotrifluoride in place of 2-chloro-5-nitrobenzonitrile. The product obtained had a melting point of 173°–5° C. On recrystallization from carbon tetrachloride and then methanol, a deep purple crystalline product was obtained.

Calcd. for $C_{18}H_{13}F_3N_2O_2$: %C, 62.4; %H, 3.78; %N, 8.08; %F, 16.46; Found: %C, 62.4; %H, 3.7; %N, 8.8; %F, 16.3.

IR spectra were consistent with the structure of FIG. 4. NMR peaks (expressed in δ units in parts per million and with positions designated by lower case letters in FIG. 4) are found at 8.33(a), 8.29(b), 8.02(c), 7.90(f), 7.1–7.7(h), 6.66(e), 6.39(d) and 3.60(g).

EXAMPLE 5

Figure 14:
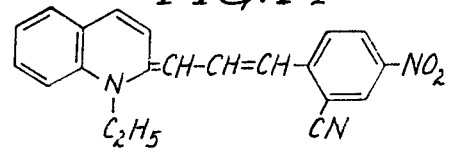
Figure 15:
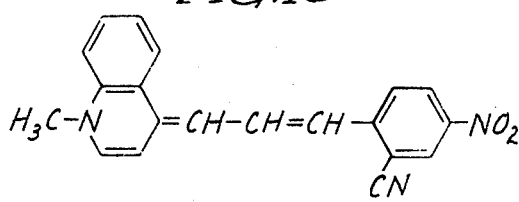
Figure 16:
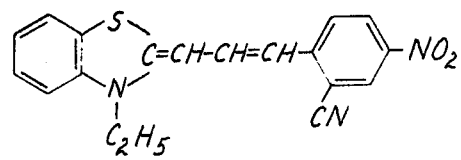
Figure 17:
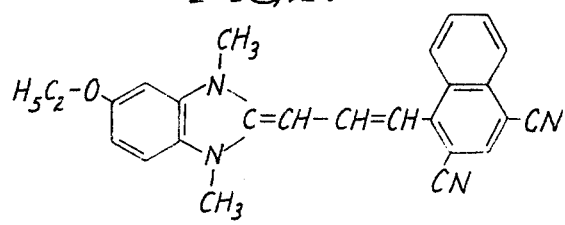
Figure 18:
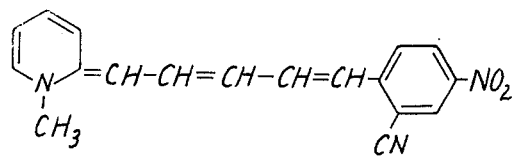
Figure 19:
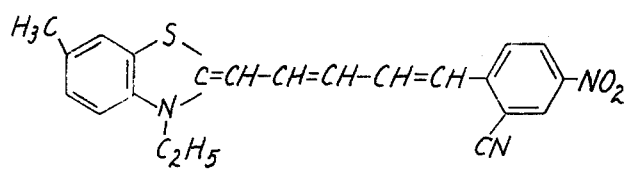
Figure 20:
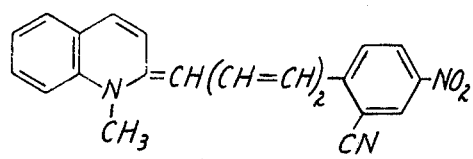
Figure 21:
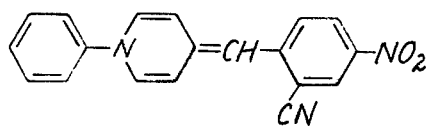
Figure 22:
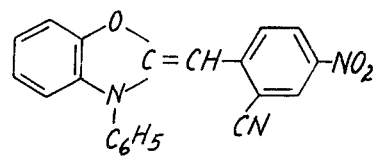
Figure 23:
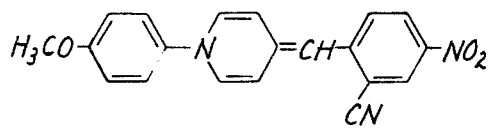
Figure 26:
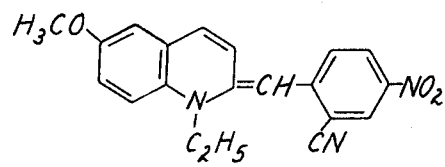
Figure 24:
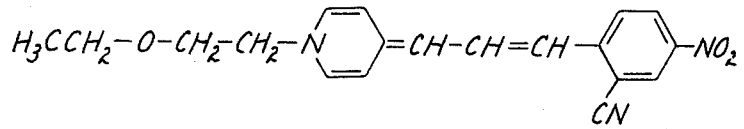
Figure 25:
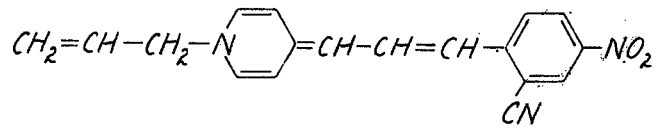

Preparation of 2-[3-(2-cyano-4-nitrophenyl)allylidene]-1-ethyl-1,2-dihydroquinoline, FIG. 14.

The condensation of 4.02 g. (0.01 mole) of 2-(2-anilinovinyl)-1-ethylquinolinium iodide (prepared as described in British Pat. No. 344,409 m.p. 263°–5° C (dec.)) with 2-cyano-4-nitrotoluene (1.67 g., 0.01 mole) was effected in 15 ml. of dimethylformamide containing 2 ml. of acetic anhydride by heating the reaction mixture to reflux, adding 1.01 g. (0.01 mole) of triethylamine, heating at reflux for 1 to 2 minutes and cooling rapidly. The precipitate was collected, washed successively with dimethylformamide, water and ether and then dried to yield 47% of theory of blue dye base m.p. 250°–252° C.

Calcd. for $C_{21}H_{17}N_3O_2$: %C, 73.4; %H, 4.98; %N, 12.33; Found: %C, 72.4; %H, 4.9; %N, 12.2.

IR spectrum was consistent with the structure of FIG. 14 but also indicated the sample to be contaminated with dimethylformamide.

When 2-(2-anilinovinyl)-1-ethylquinolinium iodide used above is replaced by 4-(4-anilinobutadien-1,3-yl)-1-methylquinolinium iodide there is obtained 4-[5-(2-cyano-4-nitrophenyl)pentadien-2,4-ylidene]-1-methyl-1,4-dihydropyridine. This arylidene dye base is chloroform is bright greenish blue having an absorption maximum of 645 to 660 nm.

The procedure of this example was repeated using equivalent quantities of the necessary quaternary compounds and 2-cyano-4-nitrotoluene to give the following compounds.

Table 1

| Structure of Dye Figure | Melting Point ° C |
|---|---|
| 13 | 240–5(dec.) |
| 14 | 250–2 |
| 15 | 235–40 (dec.) |

Table 1-continued

| Structure of Dye Figure | Melting Point ° C |
|---|---|
| 16 | 221–2 dec. (235°) |

EXAMPLE 6

A thermally developable photosensitive composition was prepared by blending in a mixing apparatus 5 g. of polyvinyl butyral and 500 g. of a dispersion of 13.8 parts by weight silver behenate in 86.2 parts by weight of a mixture in parts by volume of 68 parts methylethyl ketone, 25 parts toluene, and 7 parts methylisobutyl ketone. After the mixture had become homogeneous, it was placed under "safe" light conditions as known to those of skill in the art and 20 ml. of a solution of 1M hydrobromic acid in methanol (48% HBr diluted with methanol) was added dropwise to the vigorously stirring mixture. After stirring for 20 minutes at 25° C, 2.5 ml. of 0.15M mercuric bromide in methanol was added followed by 25 g. polyvinyl butyral and stirring was continued for 10 minutes, avoiding heat build-up as the viscosity of the mixture increased. There then was added 10 mg. of the optical sensitizer (dispersed in 10 ml. of methanol), 3-ethyl-5[(1-ethyl-1,2-dihydroquinolinylidene-2)ethylidene]-2-(3-carboxymethyl-4-oxo-2-thio-5-thiazolidinylidene)-4-thiazolidone available from Example 2 of U.S. Pat. No. 3,719,495. Other sensitizers can be used as desired. The mixture was stirred 20 minutes and 100 g. was withdrawn for preparation of a control thermally-developable material (designated A). To the remainder was added 150 mg. of the acutance dye base of Example 1 and the composition (designated B) containing acutance agent was stirred for another 30 minutes.

Both compositions, A and B, were knife coated at 125 microns onto polyester film and dried 5 minutes at 90° C in a forced draft oven. Both dried films were then topcoated at 75 microns with a developer layer composition of 81 parts methylethyl ketone, 5 parts methanol, 1.5 parts phthalazinone, 7.5 parts of bis(2,2'-dihydroxy-3,3',5,5'-tetramethyldiphenyl)-(2,4,4-trimethylpentyl)methane (available as NONOX WSO from I.C.I., Ltd.), and 5 parts of vinyl chloride/vinyl acetate copolymer (available as VYNS from Union Carbide). Films of this type are of relatively high contrast values. The topcoated films are dried 5 minutes at 90° C.

Portions of each of the films, Film A (the control not containing acutance agent) and Film B (containing acutance agent), were contact exposed through a mask overlaid with a 0–4 continuous density wedge to tungsten illumination modulated by a 560 nm. narrow band filter. The mask had a rectangular aperture with a width of about 5.5 mm. and a length of 120 mm. The coated films were then developed by heating for 16 seconds at 125° C and the width of the image that formed measured in millimeters (believed to be ± 0.01 mm) at optical densities of 2 and 3 tabulated in Table 2. The comparative values obtained are indicative of the effectiveness of acutance agents.

Table 2

| Optical Density = 2.0 | | |
|---|---|---|
| Width of Mask Aperture | Width of Image | Percent Flare |

Table 2-continued

| | | | |
|---|---|---|---|
| Film A | 5.544 mm. | 5.557 mm. | 0.23 |
| Film B | 5.546 mm. | 5.546 mm. | 0.0 |

Optical Density = 3.0

| | Width of Mask Aperture | Width of Image | Percent Flare |
|---|---|---|---|
| Film A | 5.660 mm. | 6.737 mm. | 19.0 |
| Film B | 5.664 mm. | 5.664 mm. | 0.0 |

From the above data, it is apparent that incorporation of the acutance agent of the invention eliminated image flare which without the agent would amount to 0.23% of the image width at a density of 2.0 and 19% at an image density of 3.0.

EXAMPLE 7

A series of low contrast films are prepared both with and without an extensive series of acutance dyes of the invention of the structure shown in the Figures. This procedure placed the developer and phthalazinone in the image layer rather than in a separate layer as in Example 6.

A suitable vessel is charged with 750 g of a dispersion as in Example 6 of silver behenate 45 g methyl ethyl ketone and 0.75 g polyvinylbutyral and the suspension mixed at about 22° for 15 minutes at which time a mixture of 36 ml of 1.0 M HBr in methanol and 9.5 mol of 0.1 M HI in methanol is added and stirring is continued for 1 hour. To the mixture is added 5.18 ml of 0.5 M Hg Br$_2$ in methanol followed by a further 85 g of polyvinylbutyral and stirring is continued for 20 minutes. A dispersion of 0.022 g of the same sensitizer used in Example 6 in 20 ml of methyl ethylketone is added to the total mixture which is then stirred for 75 minutes before adding 24 g of the "NONOX WSO" used in Example 6 and 7.5 g of phthalazinone and stirring is continued for 10 minutes to provide the basic emulsion. Several such batches are used in subsequent tests. Controls are prepared containing 3 ml. chloroform but no acutance dye and coated at a wet level of 125$\mu$ on 75$\mu$ polyester film and after drying 3.5 minutes at 90° C overcoated with a non-functional protective wet coat of 75$\mu$ vinyl acetate/vinyl chloride (39%) in 80:20 methyl ethyl ketone: methanol dried in the same way. The controls exposed are at several different wavelengths of light through a mask as described in Example 6 developed 15 seconds at 127° C and measured at density of 3.0 for mask aperture and image width in millimeters (believed accurate to about 0.01 mm) as shown in Table 3.

Table 3

| (nm) | Width of Mask Aperture | Width of Image | Percent Flare |
|---|---|---|---|
| 540 | 5.538 | 7.027 | 27 |
| 560 | 5.559 | 7.009 | 26 |
| 620 | 5.550 | 6.766 | 22 |
| 640 | 5.562 | 7.021 | 26 |

Samples for testing acutance dyes are prepared by dispersing 40 micromoles of the dye to be tested in 3 ml chloroform in a vessel and adding 50 g aliquots of the emulsion prepared above. The vessels are shaken well three times at intervals of 10 minutes and coated as described above for the controls. Exposure is effected at various wavelengths as controlled by filters using masks as above. Table 4 shows the acutance dyes by reference to the figures together with molecular weight, weight of dyestuff (mgm per aliquot), wavelength, mask width (mm), image width at D = 3.0 and percent flare.

Table 4

| Acutance Dye Figure | Molecular Weight | Weight of Dye | λ nm | Width of Mask Aperture | Width of Image | Percent Flare |
|---|---|---|---|---|---|---|
| 1 | 253 | 10.2 | 560 | 5.549 | 6.609 | 19 |
| 2 | 346 | 13.9 | 540 | 5.567 | 6.128 | 10 |
| 3 | 303 | 12.2 | 560 | 5.542 | 6.214 | 12 |
| 5 | 303 | 12.2 | 540 | 5.569 | 6.043 | 8.5 |
| 6 | 317 | 12.7 | 540 | 5.569 | 6.190 | 11 |
| 7 | 347 | 13.9 | 560 | 5.558 | 5.989 | 7.8 |
| 9 | 347 | 15.0 | 540 | 5.567 | 6.563 | 18 |
| 12 | 277 | 11.1 | 640 | 5.570 | 6.749 | 21 |
| 14 | 343 | 13.8 | 640 | 5.550 | 6.028 | 8.6 |
| 14 | 343 | 13.8 | 620 | 5.550 | 5.935 | 7.0 |
| 15 | 329 | 13.2 | 640 | 5.570 | 6.088 | 9.3 |
| 16 | 349 | 14 | 620 | 5.548 | 6.208 | 12 |

What is claimed is:

1. A methine arylidene dye base represented by the formula:

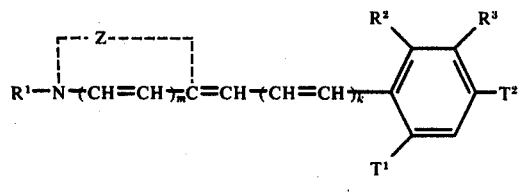

wherein:

Z represents the atom necessary to complete a mono- or polycyclic dihydroheterocyclic nucleus having 5 to 6 atoms in the ring including the N of the formula;

$R^1$ is an alkyl, substituted alkyl, alkenyl or aryl group;

$m = 0$ or 1;

$k = 0$, 1 or 2;

$T^1$ is an aprotic electron-withdrawing group having a $\sigma_{para}$ value of 0.45 to 0.63 selected from $CF_3$ and CN;

$T^2$ is $NO_2$; and $R^2$ and $R^3$ are hydrogen or together constitute a condensed carbocyclic aromatic ring.

2. A methine arylidene dye base according to claim 1 characterized by being an acutance agent wherein Z is a member of the group;

—CH=CH—, —CH=CH—CH=CH—,

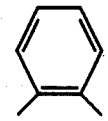

or

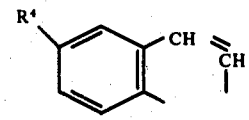

where $R^4$ is H, alkyl of 1–2 carbon atoms or alkoxy of 1–2 carbon atoms.

3. An acutance agent according to claim 2 wherein $R^1$ is alkyl of 1 to 4 carbon atoms.

* * * * *